US00PP36417P2

(12) United States Plant Patent
Volz

(10) Patent No.: US PP36,417 P2
(45) Date of Patent: Feb. 4, 2025

(54) APPLE TREE NAMED 'PremA019'

(50) Latin Name: *Malus domestica*
Varietal Denomination: PremA019

(71) Applicant: Prevar Limited, Hastings (NZ)

(72) Inventor: Richard Volz, Auckland (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 18/677,471

(22) Filed: May 29, 2024

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418; A01H 5/08
See application file for complete search history.

*Primary Examiner* — Keith O. Robinson
(74) *Attorney, Agent, or Firm* — Michelle Bos Legal LLC

(57) ABSTRACT

A new and distinct apple tree named 'PremA019' notable for its fruit, which has an attractive red skin color, appealing flavor, and large size.

5 Drawing Sheets

Latin name: *Malus domestica.*
Variety denomination: 'PremA019'.

BACKGROUND OF THE VARIETY

The new apple tree 'PremA019' was created in the course of a planned breeding program carried out at Havelock North, New Zealand. 'PremA019' originated from a controlled cross of 'Scifresh' (seed parent, U.S. Plant Pat. No. 13,888) and 'A174T01T204' (pollen parent, not patented) performed at Havelock North, New Zealand in 2009. 'PremA019' was selected from a population of seedlings derived from the parents, and was singled out for further observation for its fruit, which has an attractive red skin color and appealing flavor. The variety was first asexually propagated by grafting onto 'M9' rootstock (not patented) at Havelock North, New Zealand in 2012. 'PremA019' trees have been observed over a number of asexually propagated generations, and have been found to remain true to type.

Pollen parent 'A174R01T204' is an unpatented advanced selection from a cross performed in 1996. Both 'A174R01T204' and 'PremA019' produce large (~300 g), block-red apples, and both have the same self-incompatibility genotype, S5;S24. 'A174R01T204' is much more prone to russet than 'PremA019.' The most apparent difference is that while 'PremA019' has smooth to moderate bark, 'A174R01T204' has very distinctive rough scaly bark. This roughness is not due to disease but rather is due to genetics, and can be passed on to progeny (although 'PremA019' did not inherit it).

'PremA019' is distinguished from parent variety 'Scifresh' by its large fruit. 'Scifresh', sold commercially under the Jazz® trademark, is the most similar commercial variety. Comparisons of 'PremA019' to 'Scifresh' and to commercial varieties 'Scilate' (U.S. Plant Pat. No. 20,477) and 'Braeburn' (not patented) are set forth in Table 1 below.

TABLE 1

Comparison of 'PremA019' to other Varieties

| Comparison Variety | Characteristic | In Comparison Variety | In 'PremA019' |
|---|---|---|---|
| 'Scifresh' | Fruit size | Small, 157 g | Large, 287 g |
| 'Scilate' | Fruit size | Medium, 227 g | Large, 287 g |
| 'Scilate' | Pattern of overcolor | Striped | Solid flush with narrow- to medium-width weakly-defined stripe |
| 'Braeburn' | Pattern of overcolor | Striped | Solid flush with narrow- to medium-width weakly-defined stripe |
| 'Braeburn' | Tree vigor | Low to moderate | High |

BRIEF DESCRIPTION OF THE PHOTOGRAPHS

The attached photographs of trees and fruit were taken at Havelock, New Zealand during the 2023/2024 growing season. The trees depicted were planted in 2017 and grown on 'MM106' rootstock (not patented).

BRIEF SUMMARY OF THE INVENTION

Figure 1:
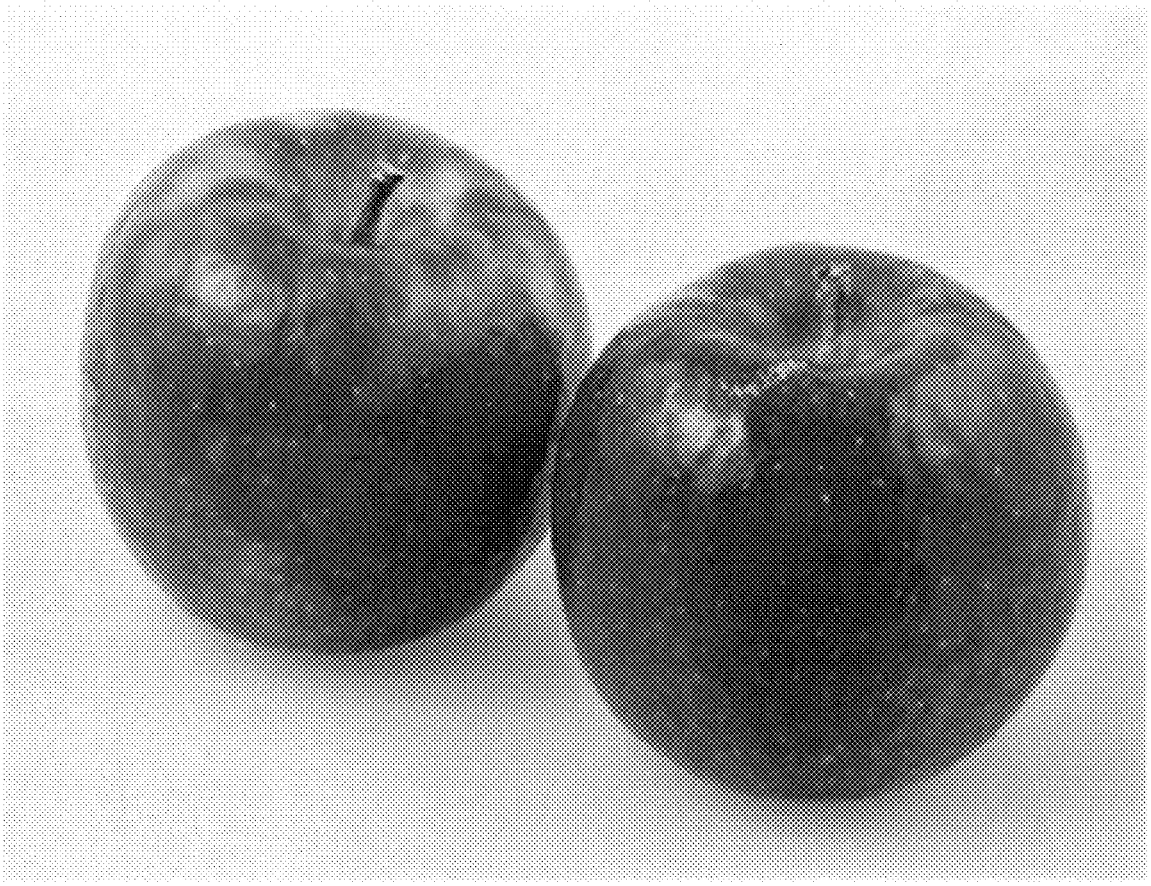
FIG. 1 shows the fruit of a 'PremA019' apple tree.
Figure 2:
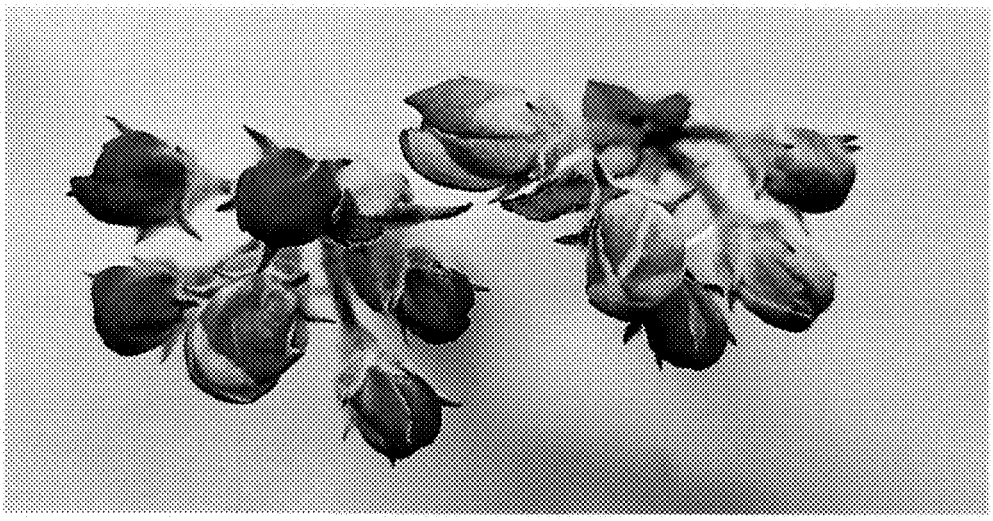
FIG. 2 shows the flower buds of a 'PremA019' apple tree.
Figure 3:
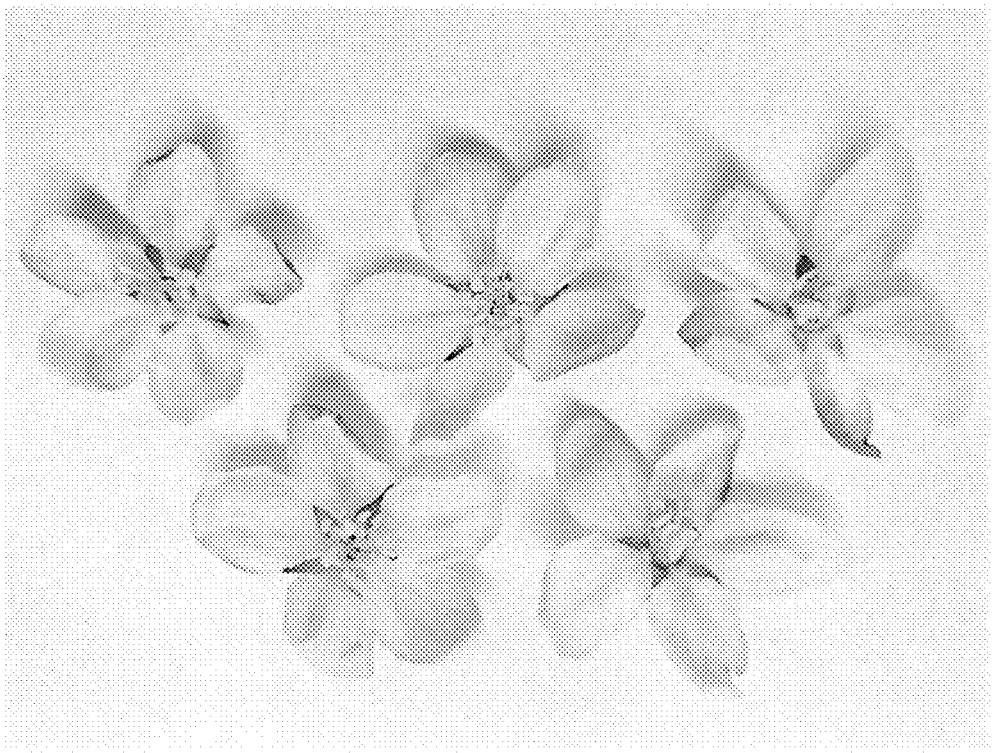
FIG. 3 shows the flowers of a 'PremA019' apple tree.
Figure 4:
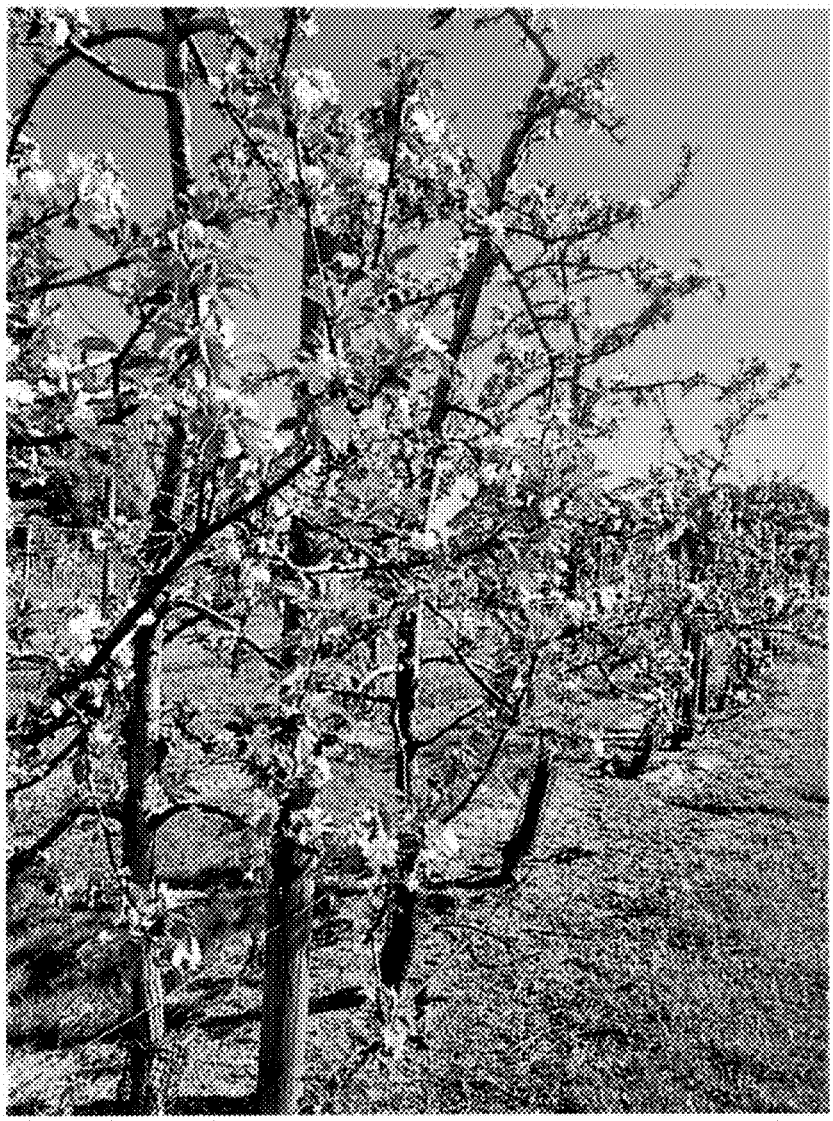
FIG. 4 shows 'PremA019' apple trees in bloom.
Figure 5:
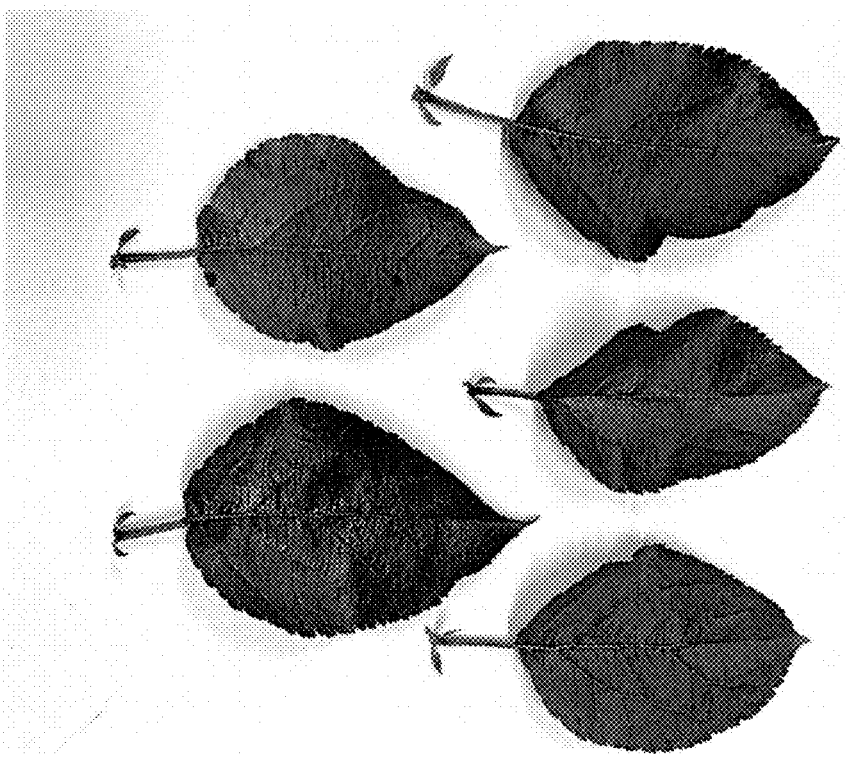
FIG. 5 shows the upper surface of leaves of a 'PremA019' apple tree.
Figure 6:
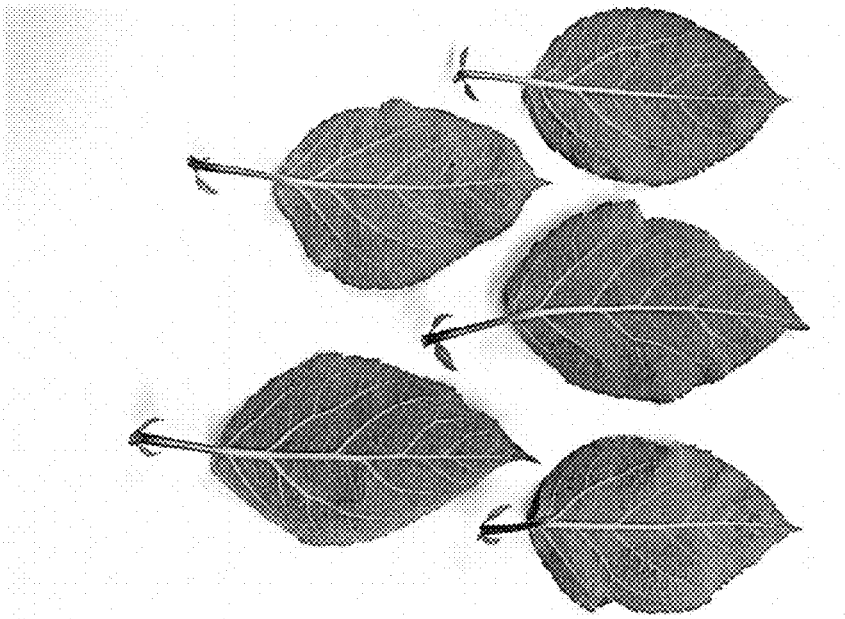
FIG. 6 shows the lower surface of leaves of a 'PremA019' apple tree.
Figure 7:
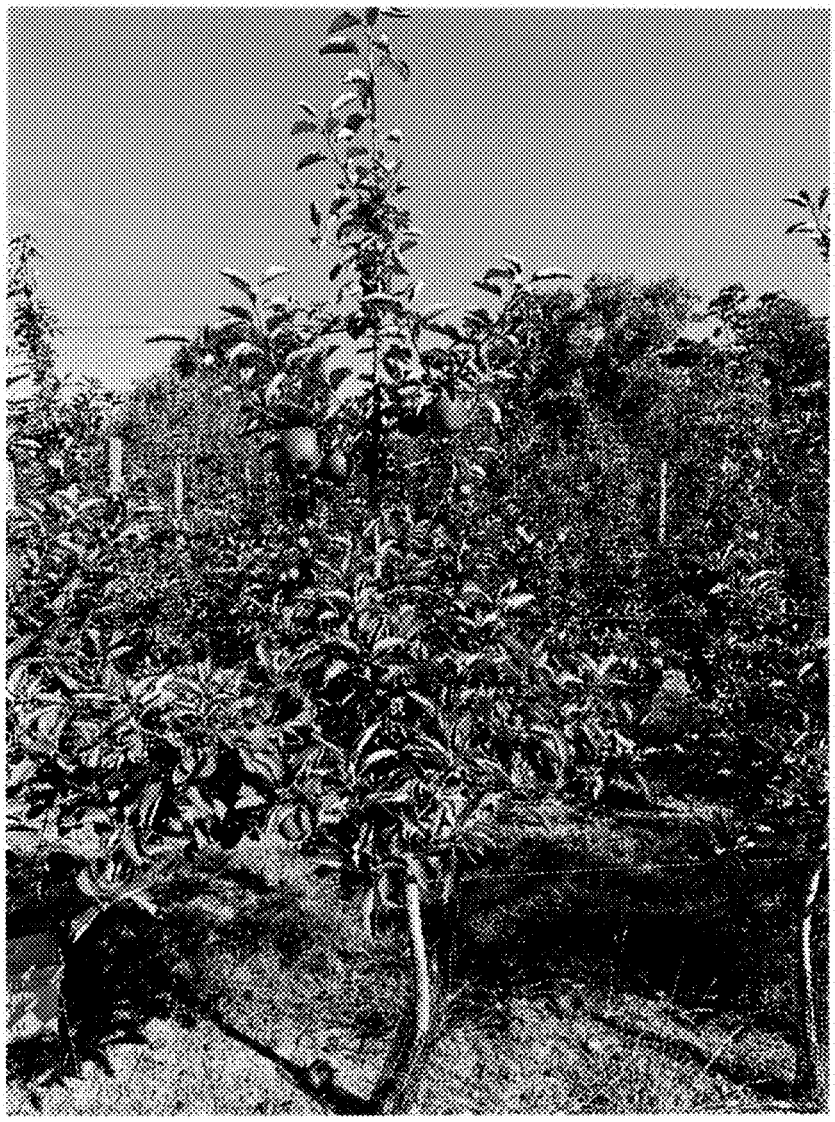
FIG. 7 shows a 'PremA019' apple tree and its fruit.

'PremA019' is a new and distinct apple tree notable for its fruit, which has an attractive red skin color, appealing flavor, and large size.

DETAILED BOTANICAL DESCRIPTION OF THE VARIETY

The following-detailed botanical description is based on trees and fruit observed at Havelock, New Zealand during the 2023/2024 growing season. The described trees were planted in 2017 and grown on 'MM106' rootstock (not patented). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average. All colors are described with reference to The R.H.S. Colour Chart, 6$^{th}$ ed. (Royal Horticultural Society, 2015).

Tree:
- *Vigor*.—High.
- *Type*.—Ramified.
- *Habit*.—Upright to spreading.
- *Height*.—3.2 m.
- *Spread*.—2.3 m.
- *Trunk diameter* (*at* 30 *cm above the graft*).—22 cm.
- *Bearing*.—On spurs.
- *Bark texture*.—Smooth to moderate.
- *Bark color*.—Grey-brown 199A.
- *Lenticel length*.—2 mm.
- *Lenticel width*.—1 mm.
- *Lenticel shape*.—Elliptic.
- *Lenticel color*.—Greyed green 195B.
- *Lenticel density*.—5 to 8 per 10 cm$^2$.

Branch (fruiting branches located at around 1 m above the graft union):
- *Length*.—87 cm.
- *Diameter*.—24 mm.
- *Crotch angle*.—80° to 95° (trained).
- *Bark color*.—Grey brown N199A.
- *Branch lenticel length*.—1.8 mm to 2.5 mm.
- *Branch lenticel width*.—1.2 mm to 1.5 mm.
- *Branch lenticel shape*.—Elongated.
- *Branch lenticel color*.—Greyed-white 156A.
- *Branch lenticel density*.—5 per cm$^2$.

One year old shoot:
- *Length*.—63 cm.
- *Diameter*.—10 mm.
- *Internode length*.—1.0 cm to 3.0 cm, average 2.33 cm.
- *Color*.—Greyed-orange 165A.
- *Pubescence*.—Present, moderate.
- *Shoot lenticel length*.—1 mm.
- *Shoot lenticel width*.—0.5 mm.
- *Shoot lenticel shape*.—Round to oblate.
- *Shoot lenticel color*.—Greyed-green 197D.
- *Shoot lenticel density*.—3 to 7 per cm$^2$.

Flower buds:
- *Stage described*.—First pink.
- *Quantity per spur*.—Average 5.
- *Bud shape*.—Obovate.
- *Apex shape*.—Rounded.
- *Length*.—10.6 mm.
- *Diameter*.—8 mm.
- *Color*.—Red-purple 61B.

Flowers:
- *Diameter of fully open flower*.—47 mm.
- *Depth of fully open flower*.—15 mm.
- *Relative position of petal margins*.—Overlapping.
- *Date of first bloom*.—Sep. 28 (2023).
- *Date of full bloom*.—Oct. 7 (2023).
- *Pollination requirement*.—Pollinator required ('Scifresh', 'Braeburn').

Petals:
- *Number per flower*.—5.
- *Petal shape*.—Obovate.
- *Length*.—21 mm.
- *Width*.—16 mm.
- *Apex shape*.—Obtuse to rounded.
- *Base shape*.—Obtuse.
- *Margin*.—Low to medium undulation.
- *Color of upper surface*.—White NN155D to red-purple 69D with purple N78C veins.
- *Color of lower surface*.—Purple 76D with purple N78B veins.

Pitsils:
- *Length*.—16 mm.
- *Color*.—Green-white 157D.

Stigma:
- *Diameter*.—<0.5 mm.
- *Color*.—Greyed-white 156C.
- *Stigma position in relation to anther*.—Above.

Style:
- *Length*.—7 mm.
- *Color*.—Yellow-green 145D.

Stamens:
- *Quantity*.—15 (mean).
- *Length*.—12 mm.
- *Anther color*.—Yellow 7A.
- *Pollen*.—Abundant, sterile.
- *Pollen color*.—Greyed-orange 165B.

Pedicel:
- *Length*.—26 mm.
- *Diameter*.—1.6 mm.
- *Color*.—With pubescence removed, primary color yellow-green 146B with secondary color yellow-green 152A.

Sepals:
- *Quantity*.—5.
- *Color*.—Yellow-green 145B.
- *Shape*.—Acute triangular, variable.
- *Apex shape*.—Acute.
- *Margin*.—Entire.

Leaves:
- *Shape*.—Ovate.
- *Length*.—10 cm.
- *Width*.—6 cm.
- *Blade margin*.—Serrate.
- *Apex*.—Acuminate.
- *Base shape*.—Rounded.
- *Color of upper surface*.—Green N137B.
- *Color of lower surface*.—Yellow-green 147C.
- *Pubescence*.—Strongly present on lower surface.
- *Attitude in relation to shoot*.—Upward.

Petiole:
- *Length*.—31 mm.
- *Diameter*.—2 mm.
- *Color*.—Yellow-green 147C with purple N79C anthocyanin coloration at base.

Fruit:
- *Quantity per cluster*.—2 to 3 (after thinning).
- *Diameter*.—87 mm.
- *Height*.—70 mm.

*Weight.*—287 g.
*General shape in profile.*—Globose.
*Position of maximum diameter.*—Near equator.
*Ribbing.*—Moderate.
*Crowning at calyx end.*—Weak.
*Size of eye.*—Medium to large.
*Aperture of eye.*—Closed to partially open.
*Depth of eye basin.*—10.4 mm.
*Width of eye basin.*—33.5 mm.
*Length of sepal.*—2.5 mm to 4 mm.
*Bloom of skin.*—Present, moderate.
*Greasiness of skin.*—Absent or weak.
*Background color of skin.*—Yellow-green 151C.
*Amount of over color.*—Large to very large, 90%.
*Over color of skin.*—Red 46A to red 46D.
*Intensity of over color.*—Intense.
*Pattern of over color.*—Solid flush with weakly defined narrow — to medium — width stripe.
*Number of lenticels.*—Moderate to abundant, 5.74 per $cm^2$.
*Size of lenticels.*—Small to medium, <1 mm.
*Amount of russet around stalk cavity.*—Absent or small.
*Amount of russet on cheeks.*—Absent or small.
*Area of russet around eye basin.*—Absent or small.
*Length of stalk.*—Short, 16 mm.
*Thickness of stalk.*—3 mm.
*Depth of stalk cavity.*—18 mm.
*Width of stalk cavity.*—41 mm.
*Stalk color.*—Greyed-orange 166B.
*Firmness of flesh.*—Firm, 8.6 $kgf/cm^2$.
*Flesh texture.*—Fine to medium.
*Juiciness.*—Juicy to very juicy.
*Aroma.*—Weak.
*Brix.*—12.4° Brix.
*Flesh color.*—Yellow-green 150D.

Seeds:
*Quantity per fruit.*—Average <1 viable seed per fruit.
*Shape.*—Ovate, symmetrical.
*Length.*—6.5 mm to 10 mm.
*Width.*—2.8 mm to 5 mm.
*Color.*—Viable seed: greyed-purple N186C. Non-viable seed: greyed-yellow 162C.

Harvest:
*Time for harvest.*—Mar. 14 (2024, Havelock North, New Zealand); after 'Royal Gala' (U.S. Plant Pat. No. 4,121).
*Number of picks.*—One.
*Yield per tree.*—80 to 100+ fruits.
*Disease and pest resistance.*—Unknown.
*Storage characteristics.*—3 months in regular air storage; 5 to 6 months in MCP storage; unknown in controlled atmosphere storage.
*Market use.*—Fresh.

I claim:

1. A new and distinct apple tree named 'PremA019', substantially as described and illustrated herein.

* * * * *